US00PP34860P2

(12) United States Plant Patent
Growns

(10) Patent No.: US PP34,860 P2
(45) Date of Patent: Dec. 20, 2022

(54) ***ANIGOZANTHOS* PLANT NAMED 'KPMASQ'**

(50) Latin Name: ***Anigozanthos* hybrid**
Varietal Denomination: KPMASQ

(71) Applicant: Digby Growns, Perth (AU)

(72) Inventor: Digby Growns, Perth (AU)

(73) Assignee: Botanic Gardens and Parks Authority

( * ) Notice: Subject to any disclaimer, the term of this patent is extended or adjusted under 35 U.S.C. 154(b) by 0 days.

(21) Appl. No.: 17/721,468

(22) Filed: Apr. 15, 2022

(51) Int. Cl.
*A01H 5/02* (2018.01)
*A01H 6/00* (2018.01)

(52) U.S. Cl.
USPC ..... Plt./362
CPC ..... *A01H 6/00* (2018.05)

(58) Field of Classification Search
USPC ..... Plt./362
CPC ..... A01H 5/02
See application file for complete search history.

(56) References Cited

PUBLICATIONS https://www.ramm.com.au/product/masquerade/; May 16, 2022; 1 page.*
https://westernindependent.com.au/2022/03/10/truly-blue-kangaroo-paws-hit-perth-shelves/; Mar. 10, 2022; 3 pages.*

* cited by examiner

*Primary Examiner* — Kent L Bell
(74) *Attorney, Agent, or Firm* — Cassandra Bright

(57) ABSTRACT

A new and distinct cultivar of *Anigozanthos* plant named 'KIPMASQ' is disclosed, characterized by a distinctive blue and red-purple colored hairs on floral structures. Foliage is short and flowering stems have very strong anthocyanin coloration. Flowering begins very early to early. The new variety is a *Anigozanthos*, typically produced as a garden or container plant.

2 Drawing Sheets

Latin name of the genus and species: *Anigozanthos* hybrid.

Variety denomination: 'KPMASQ'.

BACKGROUND OF THE INVENTION

The new cultivar is a product of a planned breeding program. The new variety originated as the result of the crossing made during July 2017 of the female parent, an unpatented, proprietary *Anigozanthos* referred to as '15/267A' and the pollen parent, an unpatented, proprietary *Anigozanthos* referred to as '15/420A'. 'KPMASQ' was discovered and selected by the inventor at a research greenhouse in New South Wales, Australia during 2018.

Asexual reproduction of the new cultivar 'KPMASQ' was in New South Wales, Australia at a research laboratory by tissue culture during 2018. 'KPMASQ' has since produced several generations and has shown that the unique features of this cultivar are stable and reproduced true to type.

SUMMARY OF THE INVENTION

The cultivar 'KPMASQ' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KPMASQ'. These characteristics in combination distinguish 'KPMASV' as a new and distinct *Anigozanthos* cultivar:

1. Short foliage.
2. Very early to early flowering.
3. Very strong anthocyanin coloration in flowering stem.
4. Distinct blue and red-purple hairs on floral structures.

PARENTAL COMPARISON

Plants of the new cultivar 'KPMASQ' are comparable to the seed parent in most horticultural characteristics; however, the new variety 'KPMASQ' differs in the following:

1. The new variety produces a perianth tube colored green and covered in hairs colored both blue and red-purple; the seed parent produces a purple perianth tube.

Plants of the new cultivar 'KPMASQ' are comparable to the pollen parent in most horticultural characteristics; however, the new variety 'KPMASQ' differs in the following:

1. The new variety produces a perianth tube colored green and covered in hairs colored both blue and red-purple; the pollen parent produces a teal and green colored perianth tube.

COMMERCIAL COMPARISON

Plants of the new cultivar 'KPMASQ' are comparable to the commercial *Anigozanthos* variety 'KPTAIL', unpatented. The two *Anigozanthos* varieties are similar in most horticultural characteristics; however, the new variety 'KPMASQ' differs in the following:

1. Anthocyanin coloration of flower stem is absent or weak in this comparator, flowering stems of 'KPMASQ' have a very strong anthocyanin coloration.
2. 'KPMASQ' begins flowering earlier than 'KPTAIL'.

BRIEF DESCRIPTION OF THE PHOTOGRAPHS

Figure 1:
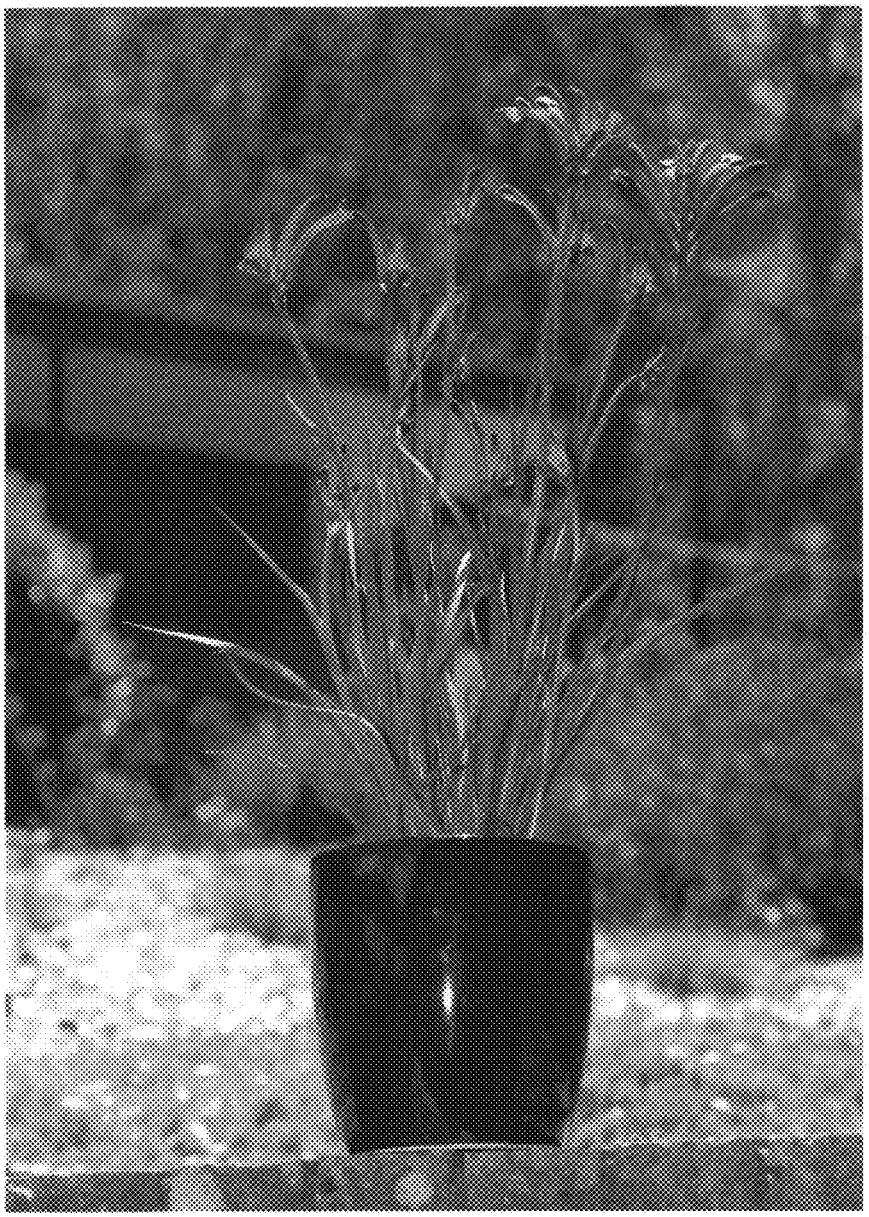

The accompanying photograph in FIG. 1 illustrates in full color a typical plant of 'KPMASQ' grown outdoors in Kangy Angy, NSW, Australia. This plant is approximately 15 weeks old, shown in a 14 cm pot.

Figure 2:
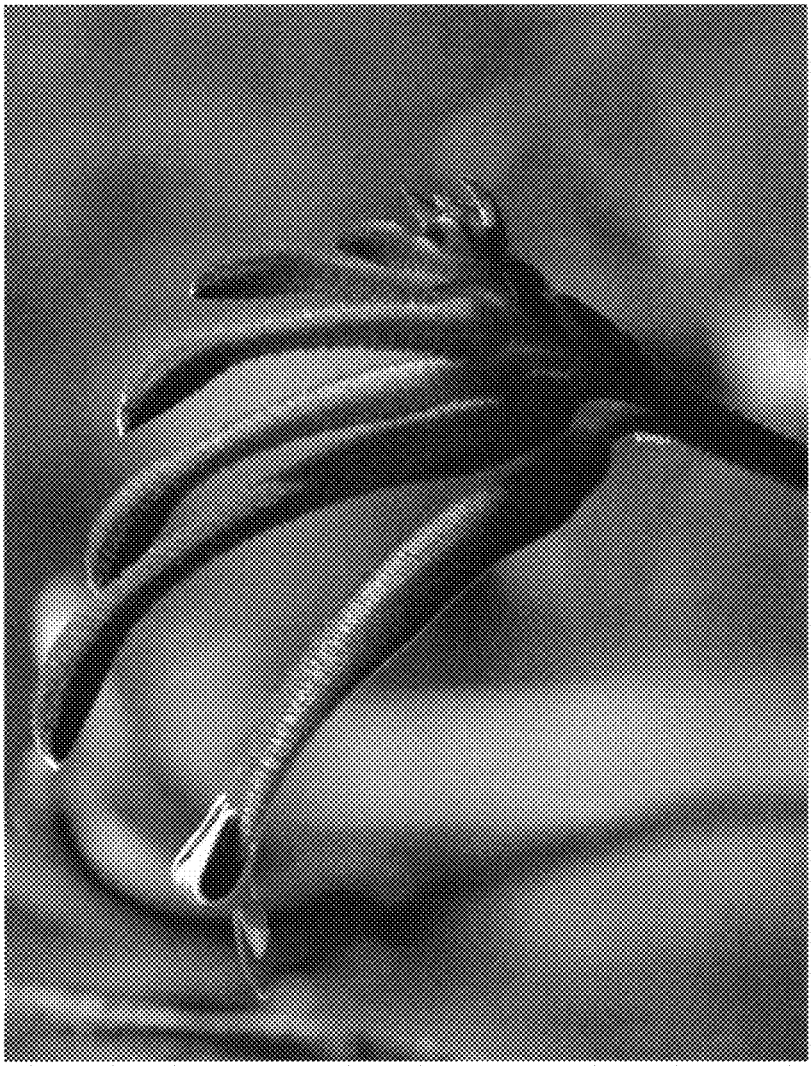

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2016, except where general terms of ordinary dictionary significance are used. The following observations and measurements describe 'KPMASQ' plants grown outdoors in full sun in Kangy Angy, NSW, Australia. Temperatures ranged from 20° C. to 32° C. during the day and 5° C. to 15° C. at night. No artificial light, photoperiodic treatments or chemical treatments were given to the plants. Measurements and numerical values represent averages of typical plant types.

Botanical classification: *Anigozanthos* hybrid 'KPMASQ'.

PROPAGATION

Time to initiate roots: 10 to 21 days at approximately 22° C. to 24° C.

Time for produce a rooted liner: 28 to 36 days at approximately 24° C. to 26° C.

PLANT

Age of plant described: Approximately 15 weeks from a rooted plantlet.

Growth habit: Compact upright fan shaped perennial with basal only branching.

Pot size: 14 cm.

Plant type: Compact upright flowering perennial.

Plant habit: Upright growing stems emerge basally.

Plant spread: Approximately 25 cm.

Height:

- *Top of foliar plane.*—22 cm.
- *Top of flowering plane.*—40 cm.

Growth rate: Moderate.

Description of roots (general thickness, color, vigor, production characteristics): Thick fleshy, main roots with fine hairs and a fibrous network of smaller roots. Colored near RHS 155B Yellowish White and 164B Moderate orange yellow.

FOLIAGE

Leaf:

- *Arrangement.*—Basally emerging, irregular rosette. Primarily fan-shaped.
- *Average length.*—22 cm.
- *Average width.*—Approximately 5 mm.
- *Shape of blade.*—Subulate.
- *Leaves per plant.*—Average 25 to 35.
- *Apex.*—Acuminate.
- *Base.*—Clasping.
- *Attachment.*—Sessile.
- *Margin.*—Entire.
- *Texture of top surface.*—Glabrous.
- *Texture of lower surface.*—Glabrous.
- *Appearance of top surface.*—Smooth, leathery with slight shine.
- *Appearance of bottom surface.*—Smooth, leathery with slight shine.
- *Color.*—Young foliage upper side: RHS Green N138A with Red-Purple 59A anthocyanin coloration at basal section of leaf. Young foliage under side: RHS Green N138A with Red-Purple 59A anthocyanin coloration at basal section of leaf. Mature foliage upper side: RHS Green 137A with Red-Purple 59A anthocyanin coloration at basal section. Mature foliage under side: RHS Green 137A with Red-Purple 59A anthocyanin coloration at basal section.
- *Venation.*—Type: Pinnate. Venation color upper side: Near RHS Green NN137B. Venation color under side: Near RHS Green NN137B.
- *Petiole.*—Not Present.

FLOWER

Natural flowering season: Freely flowering under outdoors growing conditions with substantially continuous blooming from Spring through Autumn.

Inflorescence and flower type and habit: Ramification not present. Large flowers arranged singly on terminal racemes. Individual flowers are zygomorphic, tubular, with a curved perianth.

Inflorescence height: Approximately 40 cm.

Inflorescence width: Approximately 6 cm.

Flower longevity on plant: Individual flowers last approximately 25 days.

Approximate quantity of flowers per inflorescence: About 13 flowers and buds.

Inflorescences per plant: 10 to 15.

Persistent or self-cleaning: Persistent.

Bud:

- *Shape.*—Tubular.
- *Length.*—About 2.0 cm.
- *Diameter.*—About 0.5 cm.
- *Texture.*—Pilous.
- *Color.*—Near RHS White 155C with Blue-Green 114A on tips.

Flower size:

- *Diameter.*—Approximately 3.5 cm (apical section open).
- *Length.*—Approximately 7.5 cm.

Petals (unfused floral section):

- *Length.*—Approximately 1.2 cm.
- *Diameter.*—Approximately 0.2 cm.
- *Quantity.*—6.
- *Texture.*—Exterior covered in dense, pilous hairs. Interior glabrous.
- *Apex.*—Acute.
- *Color.*—When opening: Outer, visible surface: Near Green143C covered with dense hairs colored Blue 105A. Fully opened: Outer surface: Near Green143C covered with dense hairs colored Blue 105A. Inner surface: Near RHS Yellow-Green 144B.

Perianth tube:

- *Length.*—Approximately 5.8 cm.
- *Diameter.*—Approximately 0.8 cm.

*Texture.*—Outer texture highly pubescent, inner texture glabrous.

*Description.*—Flared distally.

*Color.*—When opening: Outer, visible surface: Background color near RHS Green 143C covered in dense hairs colored Blue 105A and Red-Purple 60B. Fully opened: Outer surface: Background color near RHS Green 143C covered in dense hairs colored Blue 105A and Red-Purple 60B. Inner surface: Near RHS Yellow-Green 144B.

Floral bracts:

*Quantity.*—10.

*Shape.*—Narrow deltoid.

*Tip.*—Acuminate.

*Base.*—Clasping.

*Texture.*—Pilous on lower surface, glabrous on upper surface.

*Length.*—Approximately 1.6 cm.

*Width.*—Approximately 0.4 cm.

*Color.*—Upper surface: Near RHS Green 143B. Lower surface: Near RHS Green 138A. Covered in hairs near Red-Purple 60B.

Peduncle:

*Length.*—Average 8 cm.

*Diameter.*—0.4 cm.

*Color.*—Near RHS Greyed-Green 194A, covered in hairs colored near Red-Purple 60B.

*Aspect.*—Straight.

*Strength.*—Very strong.

*Texture.*—Pilous.

Pedicels:

*Length.*—Average 0.8 cm.

*Diameter.*—0.2 cm.

*Color.*—Background color near RHS White N155B. Tips of hairs colored near Red-Purple 60B.

*Orientation.*—Approximately 45 degrees from peduncle.

*Strength.*—Strong.

*Texture.*—Pilous.

Sepals not present.

Nectaries not observed.

Fragrance: None.

REPRODUCTIVE ORGANS

Androecium:

Stamens:

*Number.*—6.

*Filament length.*—Filaments are mostly fused to petals. Approximately 0.5 cm, unfused.

*Filament color.*—Near RHS Yellow-Green 144C.

Anthers:

*Shape.*—Ovoid.

*Length.*—Approximately 0.1 cm.

*Color.*—Near Yellow-Green 144A.

*Pollen.*—Color: RHS Yellow 11A. Quantity: Moderate.

Gynoecium:

Pistil:

*Number.*—1.

*Length.*—Approximately 5.0 cm.

*Style.*—Length: Approximately 4.8 cm. Color: Near RHS Yellow-Green 144A.

*Stigma.*—Shape: Rounded. Length: Approximately 0.1 cm. Color: Near RHS Yellow-Green 144B. Ovary Color: RHS Red-Purple 60B.

OTHER CHARACTERISTICS

Seeds and fruits: Not observed to date.

Disease/pest resistance: Neither resistance nor susceptibility to the normal diseases and pests of *Anigozanthos* has been observed.

Temperature tolerance: From approximately 0° C. to more than 40° C.

What is claimed is:

1. A new and distinct cultivar of *Anigozanthos* plant named 'KPMASQ' as herein illustrated and described.

* * * * *